(12) United States Patent
Gustine et al.

(10) Patent No.: US 9,060,815 B1
(45) Date of Patent: Jun. 23, 2015

(54) SYSTEMS AND METHODS FOR PERFORMING SPINE SURGERY

(71) Applicant: NuVasive, Inc., San Diego, CA (US)

(72) Inventors: Seth Gustine, Encinitas, CA (US); Ryan Donahoe, San Diego, CA (US); Eugene Shoshtaev, San Diego, CA (US); Spencer Pettine, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/831,696

(22) Filed: Mar. 15, 2013

Related U.S. Application Data

(60) Provisional application No. 61/679,018, filed on Aug. 2, 2012.

(51) Int. Cl.
*A61B 17/70* (2006.01)

(52) U.S. Cl.
CPC ................................. *A61B 17/705* (2013.01)

(58) Field of Classification Search
CPC ........... A61B 17/7001; A61B 17/7023; A61B 17/7032; A61B 17/7034; A61B 17/705
USPC ............ 606/246, 264–270, 272, 278, 279, 75
See application file for complete search history.

(56) References Cited

U.S. PATENT DOCUMENTS

| | | |
|---|---|---|
| 3,196,876 A | 7/1965 | Miller |
| 3,741,205 A | 6/1973 | Markolf |
| 3,788,318 A | 1/1974 | Kim |
| 3,997,138 A | 12/1976 | Crock |
| 4,047,524 A | 9/1977 | Hall |
| 4,289,123 A | 9/1981 | Dunn |
| 4,545,374 A | 10/1985 | Jacobson |
| 4,611,581 A | 9/1986 | Steffee |
| 4,620,533 A | 11/1986 | Mears |
| 4,648,388 A | 3/1987 | Steffee |
| 4,653,481 A | 3/1987 | Howland |
| 4,773,402 A | 9/1988 | Asher |
| 5,024,213 A | 6/1991 | Asher |
| 5,074,864 A | 12/1991 | Cozad |
| 5,085,660 A | 2/1992 | Lin |
| 5,108,395 A | 4/1992 | Laurain |
| 5,129,899 A | 7/1992 | Small |
| 5,137,509 A | 8/1992 | Freitas |

(Continued)

FOREIGN PATENT DOCUMENTS

| | | |
|---|---|---|
| CN | 2162921 Y | 4/1994 |
| CN | 202342145 U | 7/2012 |

(Continued)

*Primary Examiner* — Pedro Philogene
*Assistant Examiner* — David Comstock
(74) *Attorney, Agent, or Firm* — Jonathan Spangler; Rory Schermerhorn

(57) ABSTRACT

This disclosure describes example an surgical fixation system and example methods for implanting the surgical fixation system on the spine. The surgical fixation system can be applied minimally invasively to the anterior column for both single level and multi-level constructs. The surgical system can be applied to the anterior column via lateral access approaches. The lateral access approach may traverse the psoas muscle. The fixation system includes a plurality of anchor assemblies connected by a spinal rod. The anchor assemblies each include a fixation body, bone anchor, rod-receiving member, anchor lock and rod lock. The rod-receiving member may be moveably coupled to the fixation body to facilitate rod insertion.

21 Claims, 10 Drawing Sheets

(56) References Cited

U.S. PATENT DOCUMENTS

| | | |
|---|---|---|
| 5,147,360 A | 9/1992 | Dubousset |
| 5,147,361 A | 9/1992 | Ojima |
| 5,152,303 A | 10/1992 | Allen |
| 5,158,543 A | 10/1992 | Lazarus |
| 5,242,427 A | 9/1993 | Bilweis |
| 5,261,909 A | 11/1993 | Sutterlin |
| 5,306,275 A | 4/1994 | Bryan |
| 5,324,290 A | 6/1994 | Zdeblick |
| 5,330,473 A | 7/1994 | Howland |
| 5,364,399 A | 11/1994 | Lowery |
| 5,368,594 A | 11/1994 | Martin |
| 5,380,323 A | 1/1995 | Howland |
| 5,380,324 A | 1/1995 | Muller |
| 5,380,325 A | 1/1995 | Lahille |
| 5,401,247 A | 3/1995 | Yoon |
| 5,445,617 A | 8/1995 | Yoon |
| 5,476,467 A | 12/1995 | Benoist |
| 5,520,690 A | 5/1996 | Errico |
| 5,549,608 A | 8/1996 | Errico |
| 5,569,289 A | 10/1996 | Yoon |
| 5,573,511 A | 11/1996 | Yoon |
| 5,603,714 A | 2/1997 | Kaneda |
| 5,613,968 A | 3/1997 | Lin |
| 5,620,443 A | 4/1997 | Gertzbein |
| 5,662,652 A | 9/1997 | Schafer |
| 5,662,653 A | 9/1997 | Songer |
| 5,665,072 A | 9/1997 | Yoon |
| 5,667,509 A | 9/1997 | Westin |
| 5,672,176 A | 9/1997 | Harms et al. |
| 5,681,312 A | 10/1997 | Yuan |
| 5,690,629 A | 11/1997 | Asher |
| 5,697,947 A | 12/1997 | Wolf |
| 5,702,395 A | 12/1997 | Hopf |
| 5,704,936 A | 1/1998 | Mazel |
| 5,713,898 A | 2/1998 | Stucker |
| 5,713,900 A | 2/1998 | Benzel |
| 5,728,127 A | 3/1998 | Asher |
| 5,766,254 A | 6/1998 | Gelbard |
| 5,772,678 A | 6/1998 | Thomason |
| 5,800,435 A | 9/1998 | Errico |
| 5,842,478 A | 12/1998 | Benderev |
| 5,882,350 A | 3/1999 | Ralph |
| 5,899,902 A | 5/1999 | Brown |
| 5,899,904 A | 5/1999 | Errico |
| 5,899,905 A | 5/1999 | Errico |
| 5,925,047 A | 7/1999 | Errico |
| 5,928,233 A | 7/1999 | Apfelbaum |
| 5,928,243 A | 7/1999 | Guyer |
| 5,947,969 A | 9/1999 | Errico |
| 5,976,135 A | 11/1999 | Sherman |
| 5,976,146 A | 11/1999 | Ogawa |
| 6,004,322 A | 12/1999 | Bernstein |
| 6,033,420 A | 3/2000 | Hahnen |
| 6,063,090 A | 5/2000 | Schlapfer |
| 6,066,140 A | 5/2000 | Gertzbein |
| 6,083,224 A | 7/2000 | Gertzbein |
| 6,090,110 A | 7/2000 | Metz-Stavenhagen |
| 6,117,135 A | 9/2000 | Schläpfer |
| 6,123,706 A | 9/2000 | Lange |
| 6,126,660 A | 10/2000 | Dietz |
| 6,126,691 A | 10/2000 | Kasra |
| 6,132,431 A | 10/2000 | Nilsson |
| 6,136,000 A | 10/2000 | Louis |
| 6,136,002 A | 10/2000 | Shih |
| 6,152,927 A | 11/2000 | Farris |
| 6,176,861 B1 | 1/2001 | Brumfield et al. |
| 6,179,838 B1 | 1/2001 | Fiz |
| 6,187,005 B1 | 2/2001 | Brace |
| 6,206,879 B1 | 3/2001 | Marnay |
| 6,214,006 B1 | 4/2001 | Metz-Stavenhagen |
| 6,224,602 B1 | 5/2001 | Hayes |
| 6,234,705 B1 | 5/2001 | Troxell |
| 6,254,603 B1 | 7/2001 | Gertzbein |
| 6,261,265 B1 | 7/2001 | Mosseri |
| 6,261,288 B1 | 7/2001 | Jackson |
| 6,280,445 B1 | 8/2001 | Johnson et al. |
| 6,283,967 B1 | 9/2001 | Kumar et al. |
| 6,287,308 B1 | 9/2001 | Drewry et al. |
| 6,296,643 B1 | 10/2001 | Hopf |
| 6,299,613 B1 | 10/2001 | Ogilvie |
| 6,379,357 B1 | 4/2002 | Bernstein |
| 6,395,007 B1 | 5/2002 | Bhatnagar |
| 6,416,515 B1 | 7/2002 | Wagner |
| 6,447,483 B1 | 9/2002 | Steube |
| 6,471,704 B2 | 10/2002 | Gertzbein |
| 6,471,706 B1 | 10/2002 | Schumacher |
| 6,482,207 B1 | 11/2002 | Errico |
| 6,488,682 B2 | 12/2002 | Kikuchi |
| 6,524,311 B2 | 2/2003 | Gaines |
| 6,524,315 B1 | 2/2003 | Selvitelli |
| 6,533,786 B1 | 3/2003 | Needham |
| 6,533,787 B1 | 3/2003 | Lenke |
| 6,537,276 B2 | 3/2003 | Metz-Stavenhagen |
| 6,551,320 B2 | 4/2003 | Lieberman |
| 6,565,569 B1 * | 5/2003 | Assaker et al. ............... 606/250 |
| 6,569,164 B1 | 5/2003 | Assaker |
| 6,572,622 B1 | 6/2003 | Schäfer |
| 6,576,016 B1 | 6/2003 | Hochshuler |
| 6,585,740 B2 | 7/2003 | Schläpfer |
| 6,602,254 B2 | 8/2003 | Gertzbein |
| 6,616,669 B2 | 9/2003 | Ogilvie |
| 6,623,484 B2 | 9/2003 | Betz |
| 6,626,906 B1 | 9/2003 | Young |
| 6,641,564 B1 | 11/2003 | Kraus |
| 6,641,614 B1 | 11/2003 | Wagner |
| 6,645,207 B2 | 11/2003 | Dixon |
| 6,652,525 B1 | 11/2003 | Assaker |
| 6,656,179 B1 | 12/2003 | Schaefer |
| 6,663,631 B2 | 12/2003 | Kuntz |
| 6,669,700 B1 | 12/2003 | Farris |
| 6,702,817 B2 | 3/2004 | Beger |
| 6,706,044 B2 | 3/2004 | Kuslich |
| 6,746,450 B1 | 6/2004 | Wall |
| 6,749,612 B1 | 6/2004 | Conchy |
| 6,755,839 B2 | 6/2004 | Van Hoeck |
| 6,780,186 B2 | 8/2004 | Errico |
| 6,786,875 B2 | 9/2004 | Barker |
| 6,858,029 B2 | 2/2005 | Yeh |
| 6,872,209 B2 | 3/2005 | Morrison |
| 6,881,215 B2 | 4/2005 | Assaker |
| 6,899,714 B2 | 5/2005 | Vaughan |
| 6,902,565 B2 | 6/2005 | Berger |
| 6,916,319 B2 | 7/2005 | Munting |
| 6,916,320 B2 | 7/2005 | Michelson |
| 6,945,972 B2 | 9/2005 | Frigg |
| 6,945,975 B2 | 9/2005 | Dalton |
| 6,960,212 B2 | 11/2005 | Richelsoph |
| 6,969,390 B2 | 11/2005 | Michelson |
| 6,979,334 B2 | 12/2005 | Dalton |
| 7,001,387 B2 | 2/2006 | Farris |
| 7,001,396 B2 | 2/2006 | Glazier |
| 7,008,423 B2 | 3/2006 | Assaker |
| 7,022,085 B2 | 4/2006 | Cooke |
| 7,094,238 B2 | 8/2006 | Morrison |
| 7,115,129 B2 | 10/2006 | Heggeness |
| 7,137,984 B2 | 11/2006 | Michelson |
| 7,166,108 B2 | 1/2007 | Mazda |
| 7,172,600 B2 | 2/2007 | Beger |
| 7,172,612 B2 | 2/2007 | Ishikawa |
| 7,186,255 B2 | 3/2007 | Baynham |
| 7,241,074 B2 | 7/2007 | Thomke |
| 7,250,054 B2 | 7/2007 | Allen |
| 7,252,670 B2 | 8/2007 | Morrison |
| 7,255,699 B2 | 8/2007 | Paul |
| 7,291,151 B2 | 11/2007 | Alvarez |
| 7,311,712 B2 | 12/2007 | Dalton |
| 7,344,537 B2 | 3/2008 | Mueller |
| 7,377,923 B2 | 5/2008 | Purcell |
| 7,455,684 B2 * | 11/2008 | Gradel et al. ............... 606/246 |
| 7,491,205 B1 | 2/2009 | Michelson |
| 7,507,248 B2 | 3/2009 | Beaurain |
| 7,559,929 B2 | 7/2009 | Denti |
| 7,572,277 B2 | 8/2009 | Roussouly |
| 7,585,299 B2 | 9/2009 | Rezach |

(56) References Cited

U.S. PATENT DOCUMENTS

| | | |
|---|---|---|
| 7,601,167 B2 | 10/2009 | Lieberman |
| 7,618,430 B2 | 11/2009 | Scheib |
| 7,621,914 B2 | 11/2009 | Ralph |
| 7,637,952 B2 | 12/2009 | Landry |
| 7,641,701 B2 | 1/2010 | Kirschman |
| 7,643,884 B2 | 1/2010 | Pond |
| 7,651,497 B2 | 1/2010 | Michelson |
| 7,658,739 B2 | 2/2010 | Shluzas |
| 7,658,754 B2 | 2/2010 | Zhang |
| 7,662,185 B2 | 2/2010 | Alfaro |
| 7,666,185 B2 | 2/2010 | Ryan |
| 7,678,113 B2 | 3/2010 | Melkent |
| 7,682,392 B2 | 3/2010 | Serhan |
| 7,699,874 B2 | 4/2010 | Young |
| 7,699,876 B2 | 4/2010 | Barry |
| 7,704,270 B2 | 4/2010 | de Coninck |
| 7,704,271 B2 | 4/2010 | Abdou |
| 7,717,938 B2 | 5/2010 | Kim |
| 7,722,645 B2 | 5/2010 | Bryan |
| 7,731,734 B2 | 6/2010 | Clement |
| 7,740,633 B2 | 6/2010 | Assell |
| 7,744,635 B2 | 6/2010 | Sweeney |
| 7,763,051 B2 | 7/2010 | Labrom |
| 7,763,054 B2 | 7/2010 | Clement |
| 7,789,895 B2 | 9/2010 | Heinz |
| 7,789,897 B2 | 9/2010 | Sanders |
| 7,789,900 B2 | 9/2010 | Levy |
| 7,803,174 B2 | 9/2010 | Denis |
| 7,806,912 B2 | 10/2010 | Lawton |
| 7,842,038 B2 | 11/2010 | Haddock |
| 7,862,593 B2 | 1/2011 | Clement |
| D633,208 S | 2/2011 | Murner |
| 7,883,510 B2 | 2/2011 | Kim |
| 7,883,531 B2 | 2/2011 | de Coninck |
| 7,892,260 B2 | 2/2011 | Mahoney |
| 7,942,902 B2 | 5/2011 | Schwab |
| 7,942,907 B2 | 5/2011 | Richelsoph |
| 7,959,654 B2 | 6/2011 | Mazda |
| RE42,545 E | 7/2011 | Ralph |
| 7,988,691 B2 | 8/2011 | Schulze |
| 7,993,380 B2 | 8/2011 | Hawkes |
| 8,007,520 B2 | 8/2011 | Metz-Stavenhagen |
| 8,029,546 B2 | 10/2011 | Capote |
| 8,034,082 B2 | 10/2011 | Lee |
| 8,034,085 B2 | 10/2011 | Slivka |
| 8,052,725 B2 | 11/2011 | Biedermann |
| 8,083,778 B2 | 12/2011 | Clement |
| 8,123,749 B2 | 2/2012 | Serhan |
| 8,131,346 B2 | 3/2012 | Chesbrough |
| 8,133,283 B2 | 3/2012 | Wilson |
| 8,147,527 B2 | 4/2012 | Hoffman |
| 8,162,988 B2 | 4/2012 | Delecrin |
| 8,167,899 B2 | 5/2012 | Justis |
| 8,197,516 B2 | 6/2012 | Biyani |
| 8,202,216 B2 | 6/2012 | Melkent |
| 8,206,291 B2 | 6/2012 | Fischvogt |
| D663,030 S | 7/2012 | Murner |
| 8,211,151 B2 | 7/2012 | Schwab |
| 8,211,152 B2 | 7/2012 | Snyder |
| 8,221,457 B2 | 7/2012 | Delecrin |
| 8,221,468 B2 | 7/2012 | Gaines |
| 8,231,659 B2 | 7/2012 | Zolotov |
| 8,241,285 B2 | 8/2012 | Mullaney |
| 8,262,626 B2 | 9/2012 | Levendusky |
| 8,262,710 B2 | 9/2012 | Freedman |
| 8,298,269 B2 | 10/2012 | Null |
| 8,313,459 B2 | 11/2012 | Kiehne |
| 8,317,835 B2 | 11/2012 | Tornier |
| 8,323,318 B2 | 12/2012 | Baccelli |
| 8,323,319 B2 | 12/2012 | Mazda |
| 8,328,836 B2 | 12/2012 | Conlon |
| 8,337,527 B2 | 12/2012 | Hawkins |
| 8,361,130 B2 | 1/2013 | Daly |
| 8,382,804 B2 | 2/2013 | Thomke |
| 8,388,661 B2 | 3/2013 | Schlaepfer |
| 8,414,616 B2 | 4/2013 | Berrevoets |
| 8,430,916 B1 | 4/2013 | Winslow |
| D682,426 S | 5/2013 | Dominik |
| D683,461 S | 5/2013 | Murner |
| 8,435,267 B2 | 5/2013 | Chin |
| 8,454,658 B2 | 6/2013 | Lindner |
| 8,469,963 B2 | 6/2013 | Shoham |
| 8,470,000 B2 | 6/2013 | Trautwein |
| 8,506,598 B1 | 8/2013 | Tohmeh |
| 8,506,602 B2 | 8/2013 | Slivka |
| 8,518,087 B2 | 8/2013 | Lopez |
| 8,523,923 B2 | 9/2013 | Thomke |
| 8,568,456 B2 | 10/2013 | Black |
| 8,585,741 B2 | 11/2013 | Gabelberger |
| 2001/0001119 A1 | 5/2001 | Lombardo |
| 2001/0010000 A1 | 7/2001 | Gertzbein |
| 2002/0068940 A1 | 6/2002 | Gaines |
| 2002/0193795 A1 | 12/2002 | Gertzbein |
| 2003/0120275 A1 | 6/2003 | Lenke |
| 2003/0144665 A1 | 7/2003 | Munting |
| 2003/0171752 A1 | 9/2003 | Assaker |
| 2003/0187438 A1 | 10/2003 | Assaker |
| 2004/0138661 A1 | 7/2004 | Bailey |
| 2004/0147928 A1 | 7/2004 | Landry |
| 2004/0147929 A1 | 7/2004 | Biedermann |
| 2004/0162558 A1* | 8/2004 | Hegde et al. .................... 606/61 |
| 2004/0236333 A1 | 11/2004 | Lin |
| 2004/0254574 A1 | 12/2004 | Morrison |
| 2004/0267262 A1 | 12/2004 | Link |
| 2005/0010215 A1 | 1/2005 | Delecrin |
| 2005/0038433 A1 | 2/2005 | Young |
| 2005/0154388 A1 | 7/2005 | Roussouly |
| 2005/0171537 A1 | 8/2005 | Mazel |
| 2005/0171538 A1 | 8/2005 | Sgier |
| 2005/0277920 A1 | 12/2005 | Slivka |
| 2006/0004359 A1 | 1/2006 | Kramer |
| 2006/0004360 A1 | 1/2006 | Kramer |
| 2006/0009766 A1 | 1/2006 | Lee |
| 2006/0036250 A1 | 2/2006 | Lange |
| 2006/0052811 A1 | 3/2006 | Blanco |
| 2006/0079892 A1 | 4/2006 | Roychowdhury |
| 2006/0079899 A1 | 4/2006 | Ritland |
| 2006/0116676 A1 | 6/2006 | Gradel |
| 2006/0167455 A1 | 7/2006 | Clement |
| 2006/0206114 A1 | 9/2006 | Ensign |
| 2006/0229606 A1 | 10/2006 | Clement |
| 2006/0229616 A1 | 10/2006 | Albert |
| 2006/0241601 A1 | 10/2006 | Trautwein |
| 2006/0253118 A1 | 11/2006 | Bailey |
| 2007/0049932 A1 | 3/2007 | Richelsoph |
| 2007/0078463 A1 | 4/2007 | Malandain |
| 2007/0118124 A1 | 5/2007 | Biedermann |
| 2007/0123860 A1 | 5/2007 | Francis |
| 2007/0162006 A1 | 7/2007 | Ritland |
| 2007/0233066 A1 | 10/2007 | Rezach |
| 2007/0255305 A1 | 11/2007 | McMichael |
| 2007/0270816 A1 | 11/2007 | Rezach |
| 2007/0270817 A1 | 11/2007 | Rezach |
| 2007/0270818 A1 | 11/2007 | Rezach |
| 2007/0282365 A1 | 12/2007 | Popov |
| 2007/0299459 A1 | 12/2007 | Way |
| 2008/0051821 A1 | 2/2008 | Gephart |
| 2008/0140124 A1 | 6/2008 | Jeon |
| 2008/0177323 A1* | 7/2008 | Null et al. .................... 606/267 |
| 2008/0208257 A1 | 8/2008 | Matthys |
| 2008/0255617 A1 | 10/2008 | Cho |
| 2008/0262553 A1 | 10/2008 | Hawkins |
| 2008/0294203 A1 | 11/2008 | Kovach |
| 2008/0300630 A1 | 12/2008 | Bonnema |
| 2008/0306551 A1 | 12/2008 | Sanders |
| 2009/0099602 A1 | 4/2009 | Aflatoon |
| 2009/0131985 A1 | 5/2009 | Mazda |
| 2009/0138048 A1 | 5/2009 | Baccelli |
| 2009/0143738 A1 | 6/2009 | Hendriksen |
| 2009/0149857 A1 | 6/2009 | Culbert |
| 2009/0163942 A1 | 6/2009 | Cuevas |
| 2009/0182379 A1 | 7/2009 | Baccelli |
| 2009/0187217 A1 | 7/2009 | Weiman |
| 2009/0216242 A1 | 8/2009 | Riemer |

(56) References Cited

U.S. PATENT DOCUMENTS

| | | |
|---|---|---|
| 2009/0264926 A1 | 10/2009 | Taylor |
| 2009/0275970 A1 | 11/2009 | Leibowitz |
| 2009/0326585 A1 | 12/2009 | Baccelli |
| 2009/0326588 A1 | 12/2009 | Felix |
| 2010/0094346 A1 | 4/2010 | Matityahu |
| 2010/0094358 A1 | 4/2010 | Moore |
| 2010/0152787 A1 | 6/2010 | Walsh |
| 2010/0241171 A1 | 9/2010 | Clement |
| 2010/0324488 A1 | 12/2010 | Smith |
| 2011/0034956 A1 | 2/2011 | Mazda |
| 2011/0071569 A1 | 3/2011 | Black |
| 2011/0144687 A1 | 6/2011 | Kleiner |
| 2011/0238118 A1 | 9/2011 | Baccelli |
| 2011/0245857 A1 | 10/2011 | Stan |
| 2011/0270325 A1 | 11/2011 | Keyer |
| 2011/0319940 A1 | 12/2011 | Slivka |
| 2012/0004665 A1 | 1/2012 | Defossez |
| 2012/0022591 A1 | 1/2012 | Baccelli |
| 2012/0022592 A1 | 1/2012 | Belliard |
| 2012/0029566 A1 * | 2/2012 | Rezach ......................... 606/264 |
| 2012/0029567 A1 | 2/2012 | Zolotov |
| 2012/0065685 A1 | 3/2012 | Lee |
| 2012/0095417 A1 | 4/2012 | Justis |
| 2012/0108926 A1 | 5/2012 | Kassab |
| 2012/0197298 A1 | 8/2012 | Baccelli |
| 2012/0290010 A1 | 11/2012 | Zamani |
| 2013/0123854 A1 | 5/2013 | Kondrashov |
| 2013/0253516 A1 | 9/2013 | Mackall |
| 2013/0261668 A1 | 10/2013 | Douget |
| 2013/0268004 A1 | 10/2013 | Rathbun |
| 2013/0325070 A1 | 12/2013 | Larroque-Lahitette |

FOREIGN PATENT DOCUMENTS

| | | |
|---|---|---|
| DE | 4429744 A1 | 2/1996 |
| EP | 0888754 A1 | 1/1991 |
| EP | 0637437 A1 | 2/1995 |
| FR | 2704136 A1 | 10/1994 |
| KR | 20010112139 A | 12/2001 |
| WO | WO-9400062 | 1/1994 |
| WO | WO-9632882 | 10/1996 |
| WO | WO-9848719 | 5/1999 |
| WO | WO-0241796 | 5/2002 |
| WO | WO-03096914 | 11/2003 |
| WO | WO-2005004947 | 1/2005 |
| WO | WO-2006111852 | 10/2006 |

* cited by examiner

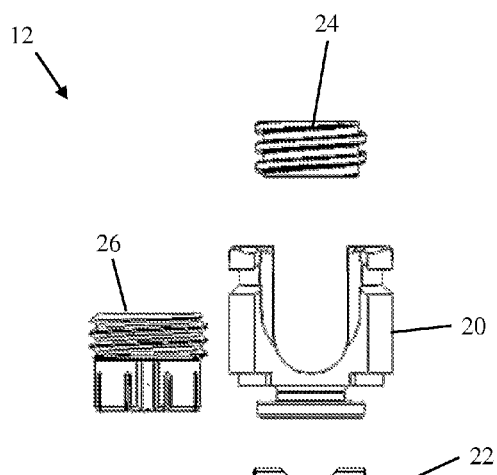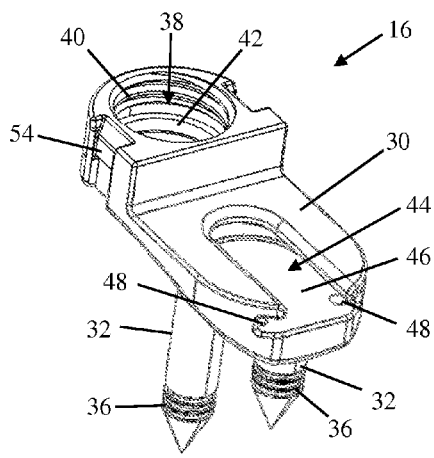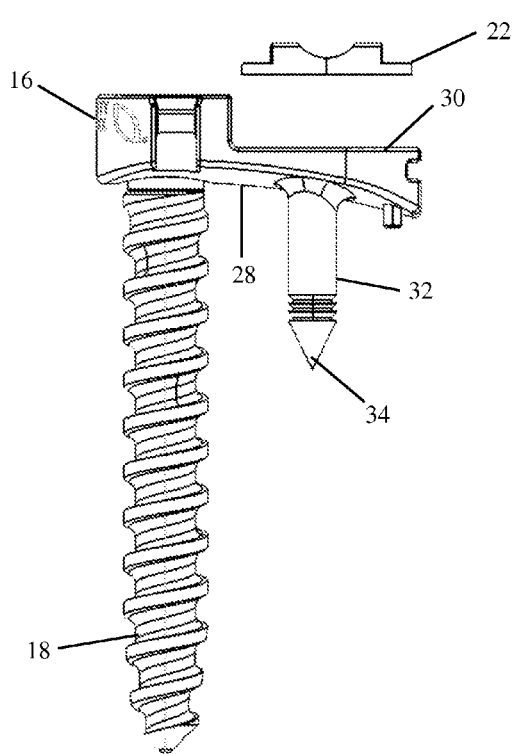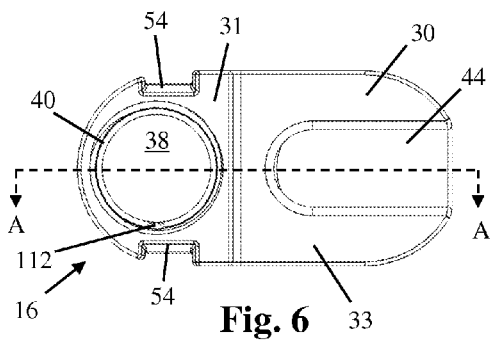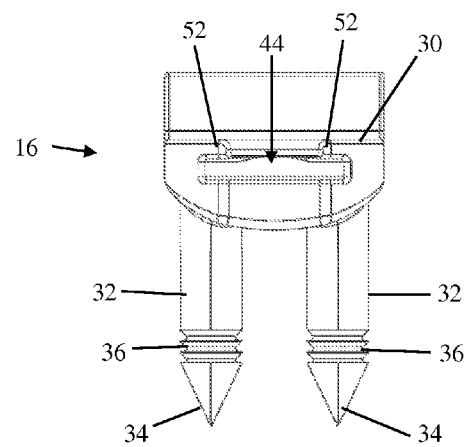
Fig. 4  Fig. 5  Fig. 6  Fig. 7

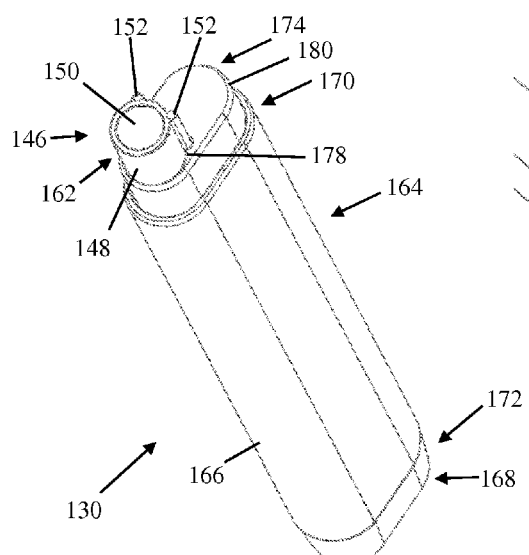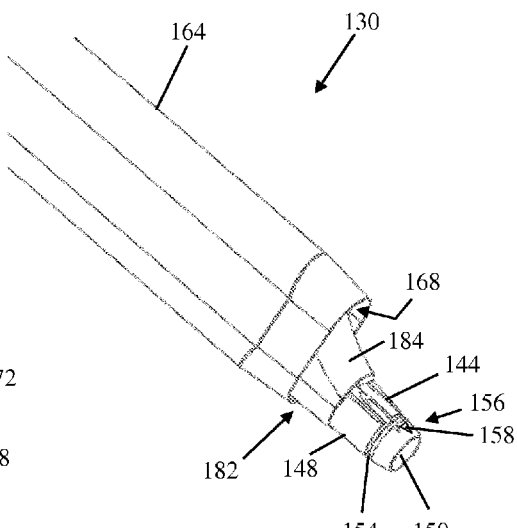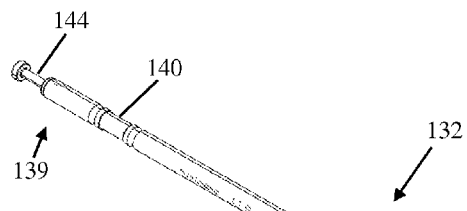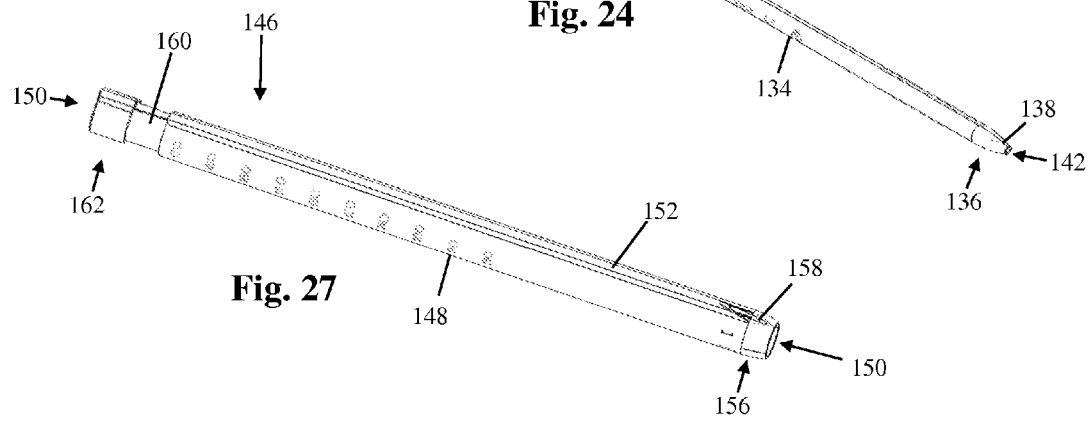

Fig. 30
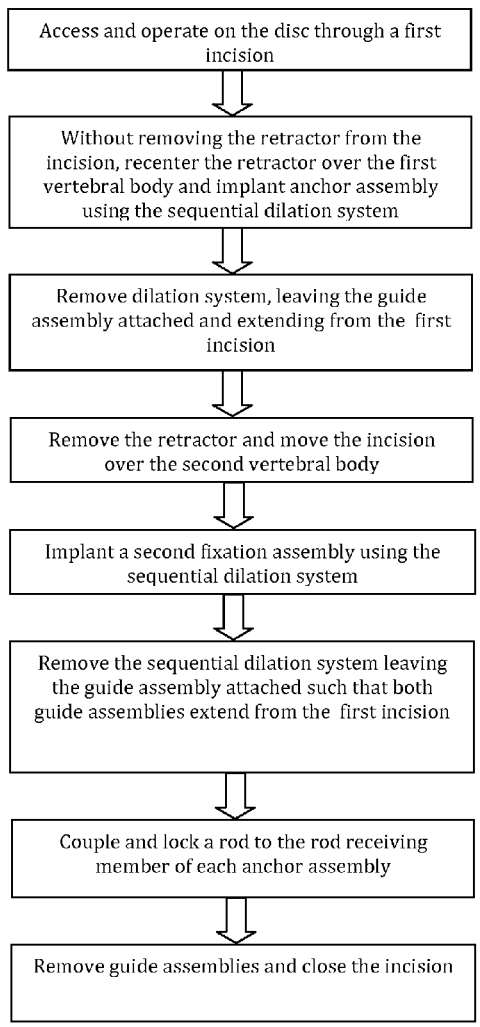
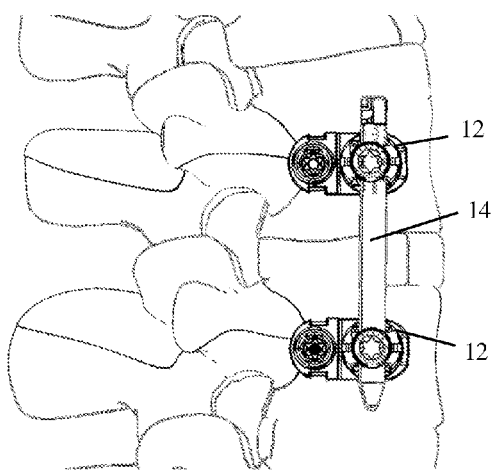
Fig. 31

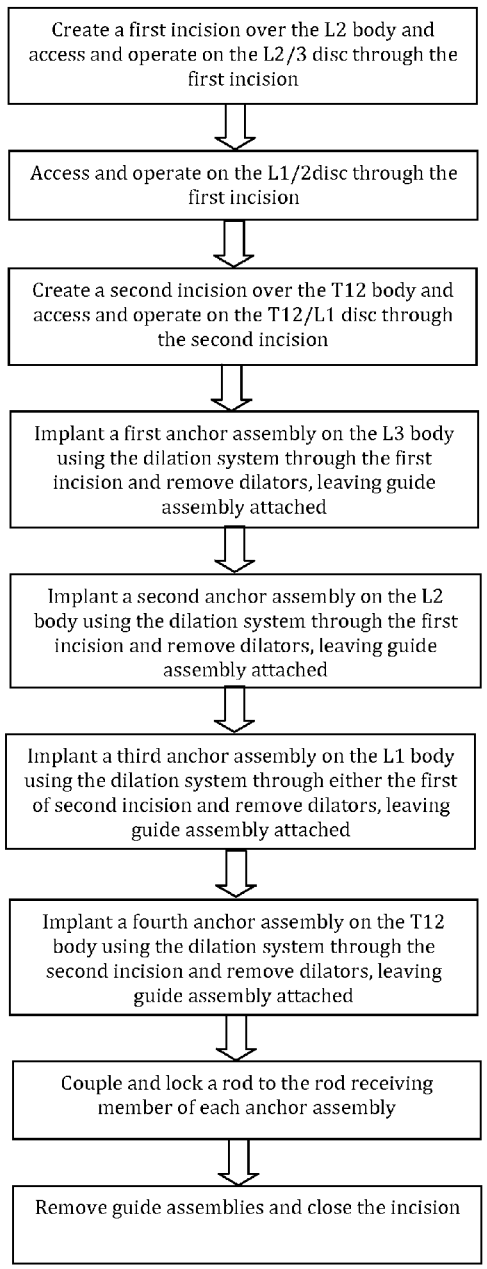
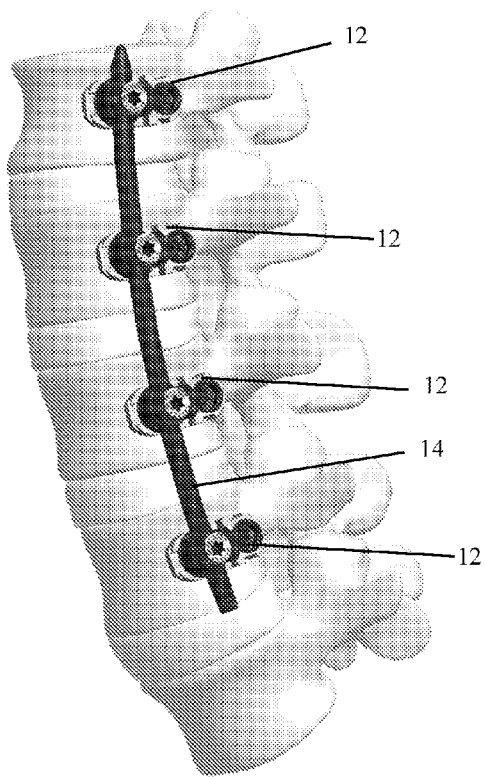
Fig. 33
Fig. 32

SYSTEMS AND METHODS FOR PERFORMING SPINE SURGERY

CROSS REFERENCES TO RELATED APPLICATIONS

The present application is a non-provisional application claiming the benefit of priority under 35 U.S.C. §119(e) from commonly owned U.S. Provisional Application Ser. No. 61/679,018 filed on Aug. 2, 2012 and entitled "Systems and Methods for Performing Spine Surgery," the entire contents of which is hereby incorporated by reference into this disclosure as if set forth fully herein. This application also incorporates by reference the entire contents of the following commonly owned Patents and Patent Applications: U.S. Pat. No. 7,905,840, issued on Mar. 15, 2011 and entitled "Surgical Access System and Related Methods;" U.S. Pat. No. 8,255,045, issued Aug. 28, 2012 and entitled "Neurophysiology Monitoring System;" U.S. patent application Ser. No. 13/415,769, filed Mar. 8, 2012 and entitled "Lateral Fixation Constructs and Related Methods;" and U.S. patent application Ser. No. 13/456,210, filed Apr. 25, 2012, and entitled "Minimally Invasive Spinal Fixation System and Related Methods."

FIELD OF INVENTION

The present application relates generally to implants, instruments, and methods for performing spinal fixation.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to treat and correct ailments of the spine.

When conservative efforts fail, treating spinal ailments very often includes a combination of spinal fusion and fixation. Generally, spinal fusion procedures involve removing some or all of an intervertebral disc, and inserting one or more intervertebral implants into the resulting disc space. Introducing the intervertebral implant serves to restore the height between adjacent vertebrae ("disc height") and maintain the height and/or correct vertebral alignment issues until bone growth across the disc space connects the adjacent vertebral bodies. Fusions may be performed across a single level or multiple levels.

Fixation systems are often surgically implanted during a fusion procedure to help stabilize the vertebrae to be fused until the fusion is complete. Fixation systems often use a combination of rods, plates, pedicle screws, and bone hooks to attach a fixation construct to the affected vertebrae. Like the fusion, the fixation system can be implanted across a single level or across multiple levels, and typically, the fixation system is positioned to span each level to be fused. Fixations systems are designed to engage either the posterior elements (e.g. pedicle screw systems, spinous process plates) or anteriorly, the vertebral bodies (e.g. plates, anterior staple/rod systems). The configuration required for each procedure and patient varies due to the ailment being treated, the specific method of treatment (e.g. surgical approach, etc. . . . ) and the patient's specific anatomical characteristics.

A trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. For example, a minimally invasive lateral (from the patients side) approach to access the disc for fusion has been developed over the last decade and demonstrated great success in reducing patient morbidity, shortening the length of hospitalization, and decreasing recovery time when employed.

Minimally invasive posterior pedicle based fixation systems are also now well known in the art and can be used in conjunction with the lateral based access for fusion when multiple levels are involved. However, this can be disadvantageous in that it generally involves repositioning the patient in between the fusion procedure and the fixation procedure. On the other hand, the availability of minimally invasive fixation systems for fixing to the anterior column is generally limited to single level procedures. Accordingly, there is a need for minimally invasive fixation systems designed to engage the anterior column across multiple levels, particularly in conjunction with a lateral access fusion procedure.

The devices and methods described in the present application address these needs.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein:

FIG. 4 is an exploded plan view of the anchor assembly of FIG. 2;

FIGS. 5-8 are perspective, top plan, side plan, and front plan views, respectively, of a fixation body forming part of the anchor assembly of FIG. 2;

FIG. 24 is a perspective view of an example sequential dilation system configured for use with the surgical fixation system of FIG. 1;

FIG. 25 is a perspective view of a distal end of the sequential dilation system of FIG. 24;

FIG. 26 is a perspective view of an initial dilator configured for use with the sequential dilation system of FIG. 24;

FIG. 27 is a perspective view of an alternate embodiment of a fixation dilator forming part of the sequential dilation system of FIG. 24;

FIG. 30 is a flowchart denoting example steps of a method for performing a surgical procedure including a single level lateral fusion with fixation using the fixation system of FIG. 1;

FIG. 31 is a plan view of a single-level surgical fixation system of FIG. 1 fully implanted on a portion of a spine;

FIG. 32 is a flowchart denoting example steps of a method for performing a surgical procedure including a multilevel lateral fusion with fixation using the fixation system of FIG. 1;

FIG. 33 is a plan view of a multilevel surgical fixation system of FIG. 1 fully implanted on a portion of a spine.

DESCRIPTION OF THE PREFERRED EMBODIMENT

Figure 1:
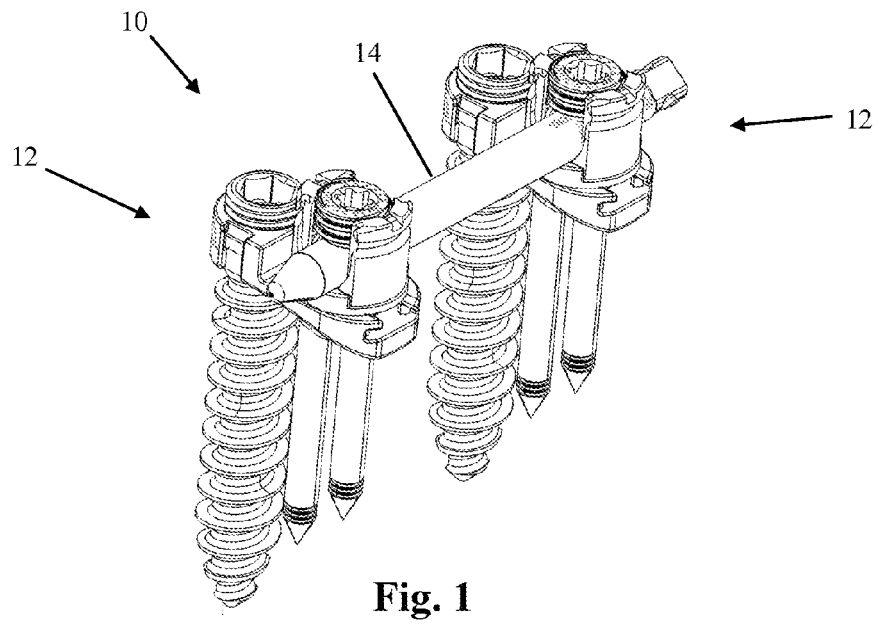
FIG. 1 is a perspective view of one example of a vertebral fixation system according to a first embodiment.
Figure 2:
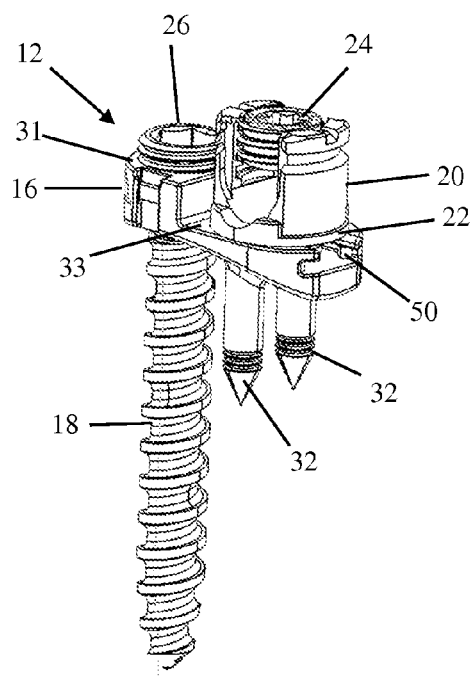
FIGS. 2 and 3 are perspective and plan views, respectively, of an anchor assembly forming part of the vertebral fixation system of FIG. 1.
Figure 3:
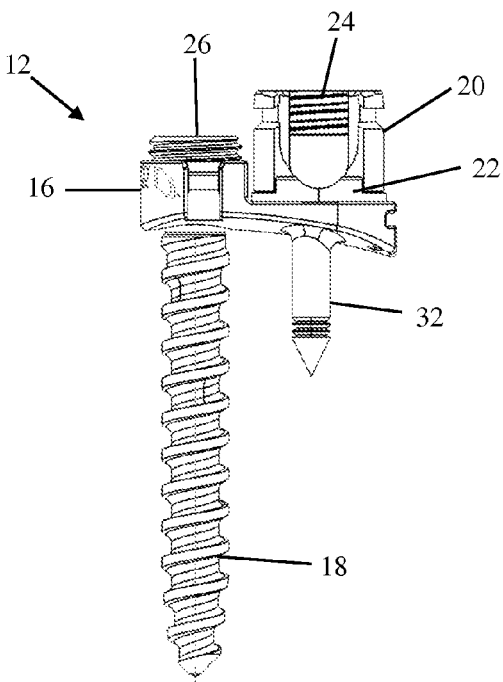
Figure 8:
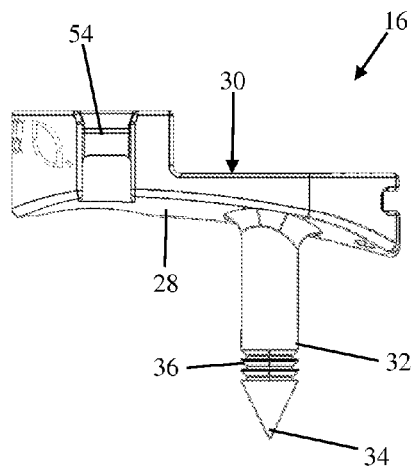
Figure 9:
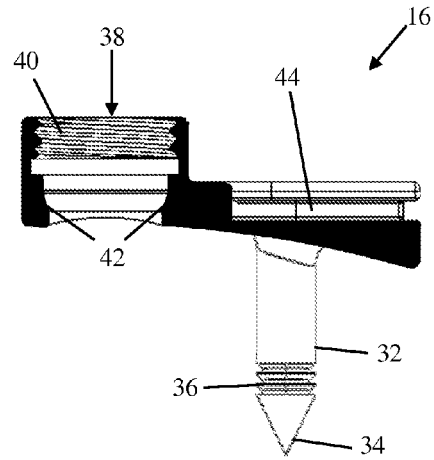
FIG. 9 is a sectional view of the fixation body of FIG. 5 taken along line A-A of FIG. 6.

Various embodiments of devices and techniques for spinal fixation are described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The vertebral fixation system and methods described herein boast a variety of inventive features and components that warrant patent protection, both individually and in combination.

FIGS. 1-4 illustrate an example of a vertebral fixation system 10 according to a first embodiment of the present invention. The vertebral fixation system 10 includes at least a pair of anchor assemblies 12 connected by a spinal rod 14. Each anchor assembly 12 includes a fixation body 16, a bone anchor 18, a rod-receiving member 20, a washer 22, rod lock 24, and an anchor lock 26. As will be explained in further detail below, the vertebral fixation system 10 is configured to allow for independent implantation of the bone anchor 18 prior to implantation of the fixation body 16 (and the rest of the construct). Furthermore, the vertebral fixation system 10 is semi-adjustable during implantation in that the rod-receiving members 20 have some freedom to translate and/or rotate relative to the fixation body 16 to accommodate insertion of the spinal rod 14, which in many cases is not strictly straight due to the specific patient's spinal structure. When the rod is appropriately implanted, the construct is locked in place by tightening the rod lock 24, which in turn causes the rod-receiving member 20 to be locked in place relative to the fixation body 16.

Referring to FIGS. 5-9, the fixation body 16 of the instant example has a generally oblong footprint. The fixation body 16 includes a first surface 28 and a second surface 30 opposite the first surface 28, the second surface 30 including an upper shelf 31 and a lower shelf 33. The first surface 28 is configured to engage the vertebral body and thus has a generally concave curvature to better fit the generally convex contour of the lateral aspect of the vertebral body. The fixation body 16 includes one or more projections 32 extending generally perpendicularly from the first surface 28 to provide purchase for the fixation body 16 within the vertebral body. By way of example, the projections 32 are provided as elongated cylindrical posts with a conical tip 34 that may be impacted into the vertebral body such that upon implantation of the fixation body 16 the first surface 28 rests flush against the lateral surface of the vertebral body. The projections 32 may be provided with additional purchase features 36 to help prevent backout of the projections 32 once implanted. In the example shown, the purchase features 36 are provided as a plurality of unidirectional tapered ridges positioned near a distal end of each projection 32. The unidirectional tapered ridges allow for insertion of the projections 32 into bone and then subsequently resist the removal of the projections 32 from the bone. According to a preferred example, the projection 32 may have a length ranging from approximately 15 mm to 40 mm and a diameter of approximately 3.5 mm. The relatively large dimension of the projection 32 provide for increased torsional and compressive stability in bone. Additionally, the projection design and anterior position on the fixation body 16 reduce risk of nerve injury since the nerves (e.g. femoral nerve) are generally located more posteriorly along the spine. Furthermore, although shown by way of example according to the preferred arrangement described above, the projections 32 may be provided in various alternative numbers and/or configurations from that shown. For example, the projections may be arranged along the perimeter of the first surface 28. The number of projections 32 may also vary from the two shown to include a single projection or many smaller projections without departing from the scope of the present disclosure.

The upper shelf 31 of the fixation body 16 includes an aperture 38 extending axially therethrough and is configured to receive the head 114 of the bone anchor 18 therein. The upper portion of the aperture 38 includes a threaded region 40 that is configured to threadedly engage the anchor lock 26. The lower portion of the aperture 38 includes a conical taper 42 around the inner circumference of the aperture 38. The conical taper 42 interacts with the flexible extensions 108 of the anchor lock 26 to force the flexible extensions 108 inward about the head 114 of the bone anchor 18. In this fashion, the anchor lock 26 forcibly engages the bone anchor 18, thereby locking the fixation body 16 to the bone anchor 18. The lower shelf 33 of upper surface 30 is a generally planar surface and includes a passage configured to allow limited translation and/or rotation of the rod-receiving member 20 relative to the fixation body 16. By way of example, when viewed from the side (FIG. 7) the passage of the example embodiment shown is a T-shaped recess 44 formed within the second surface 30. The T-shaped recess 44 is an elongated slot opening in the top surface 30 and an end of the fixation body 16. The recess 44 includes a generally planar bottom surface 46 and a pair of apertures 48 formed within the bottom surface 46 near the open end of the recess 44. The apertures 48 are configured to receive posts 50 (FIG. 2), which in this embodiment are provided to limit the translation of the rod-receiving member 20 and retain the rod-receiving member 20 within the recess 44. Other retention methods are possible however, including but not limited to (and by way of example only) laser welding, crimping, swedging, and any combination of such. A pair of overhangs 52 of the lower shelf 33 overhang the recess 44 and give the recess 44 its T-shape and retain the cylindrical flange 64 of the rod-receiving member 20 within the recess 44. The fixation body 16 further includes a pair of lateral recesses 54 positioned on opposite side surfaces of the upper shelf 31 of fixation body 16. The lateral recesses 54 are configured to receive a portion (for example engagement flanges) of an insertion tool (not shown) to allow coupling with the inserter without enlarging the profile of the assembly within the operative space.

Figure 10:
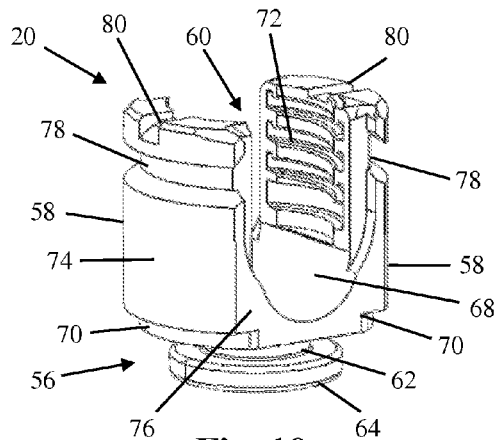
FIGS. 10-12 are perspective, side plan, and top plan views, respectively, of a rod-receiving member forming part of the anchor assembly of FIG. 2.
Figure 11:
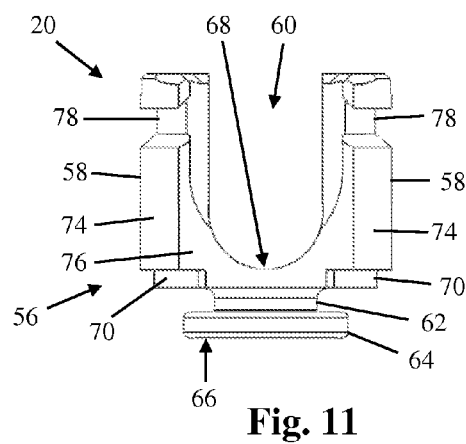
Figure 12:
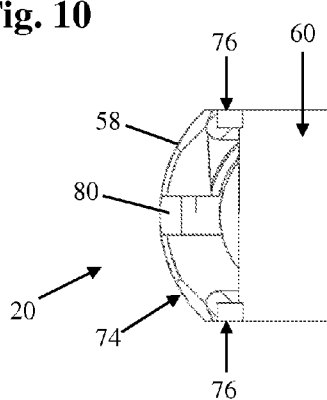

FIGS. 10-12 illustrate one example of a rod-receiving member 20 forming part of the vertebral fixation system 10. The rod-receiving member 20 includes a base 56 and a pair of upstanding arms 58 separated by a rod channel 60. The base 56 includes a protrusion 62 extending away from the base 56 and a cylindrical flange 64 positioned a the end of the protrusion 62. The protrusion 62 has a generally cylindrical shape and has a diameter that is less than the diameter of the cylindrical flange 64. The result is that the protrusion 62 and flange 64 when taken together have a generally T-shaped cross section. The protrusion 62 and flange 64 fit within the recess 44 of the fixation body 16 and are configured to allow multiple degrees of movement of the rod-receiving member 20 relative to the fixation body 16. More specifically, the cylindrical shapes of both the protrusion 62 and flange 64 allow axial rotation of the rod-receiving member, and a generally planar bottom surface 66 of the flange 64 allows for smooth translation of the flange 64 (and thus the rod-receiving member 20) within the recess 44. The upper surface 68 of the base 56 is a concave, semi-cylindrical surface having a generally arcuate cross-section. The upper surface 68 represents the distal end of the rod channel 60 and forms a cradle that receives the spinal rod 14 during implantation. The base 56 further includes a pair of undercut recesses 70 formed within the base 56 just below each of the upstanding arms 58. The undercut recesses 70 are sized and configured to receive at least a portion of the washer 22 to provide a snug interaction between the washer 22 and the rod-receiving member 20. Furthermore, the undercut recesses 70 allow for capture of the washer during assembly and facilitates rotation of the washer with the rod-receiving member due to the non-circular shape of the rod-receiving member 20.

Figure 17:
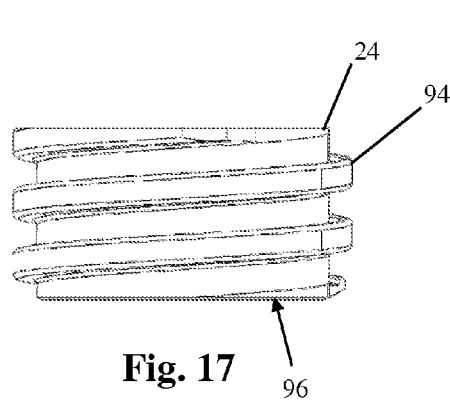
Figure 28:
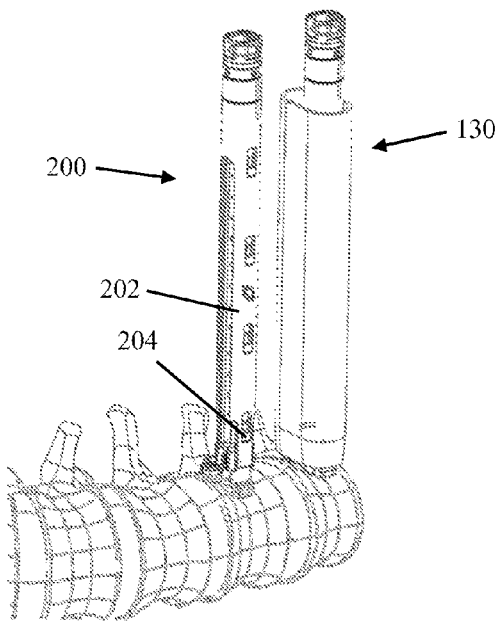
FIG. 28 is a perspective view depicting of a pair of fixation assemblies being positioned on adjacent vertebrae during construction of the fixation assembly of FIG. 1.

The upstanding arms 58 are equipped with a rod lock guide and advancement feature 72, such as by way of example, a helically wound flange feature disposed on the interior face of each arm 58. The rod lock guide and advancement feature 72 mates with a complementary guide and advancement feature 94 on the rod lock 24 (FIG. 17). The rod lock 24 engages the upstanding arms 58 via the complementary guide and advancement features 72, 94 to press and lock the spinal rod 14 into the rod-receiving member 20. The outer arcuate surfaces 74 of the upstanding arms have a convex curvature to minimize impaction of the surrounding tissue after implantation. The rod-receiving member 20 also includes a pair of opposing outer planar surfaces 76 adjacent the rod channel 60. As best viewed in FIG. 12, it is the opposing outer planar surfaces 76 that give the rod-receiving member its non-circular shape. Each upstanding arm 58 further includes an attachment groove 78, formed in the outer arcuate surface 74 near the proximal end of the upstanding arm 58. The attachment grooves 78 are dimensioned to receive engagement ridges or protrusions on the outer sleeve 202 of the guide assembly 200 to releasably lock the guide assembly 200 to the rod-receiving member 20 (FIG. 28). The top of each upstanding arm 58 further includes a recess 80 formed therein. The recesses 80 are dimensioned to receive raised protrusions on the distal end of the inner arm members 204 of the guide assembly 200. This interaction prevents rotation of the rod-receiving member 20 relative to the guide assembly 200, such that the rod receiving member rotates with the guide member. By way of example only, the guide assembly 200 may be similar to the type shown and described in commonly owned U.S. patent application Ser. No. 13/456,210, filed Apr. 25, 2012, the entire contents of which are hereby incorporated by reference into this disclosure as if set forth fully herein. Generally, the guide assembly 200 includes an outer sleeve 202 and a pair of independent arms 204 that attach to the upstanding arms 58 of the rod-receiving member 20. This allows the position of the rod-receiving member 20 to be manipulated easily from out of the incision. The guide assembly 200 uses a slot formed between opposing inner arms 204 to guide the spinal rod 14 into the rod-receiving member 20 of the fixation body 16 and to be reduced or forced into the rod-receiving member 20. In use, the fixation bodies 16 are inserted through the final dilators 164 with the guide assemblies 200 attached. Thereafter the final dilators 164 are removed leaving the guide assemblies connected to the rod-receiving member and extending out of the incision. When all fixation bodies 16 are implanted, the guide assemblies 200 are utilized to direct rod placement within the rod-receiving members of each anchor assembly 12 of the fixation construct and to facilitate insertion of rod locks 24.

Figure 13:
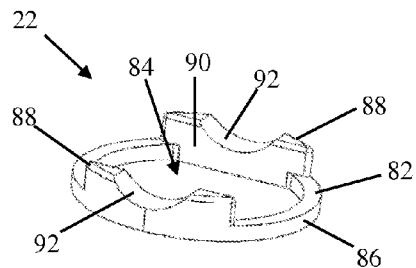
FIGS. 13-15 are perspective, side plan, and top plan views, respectively, of a washer member forming part of the anchor assembly of FIG. 2.
Figure 14:
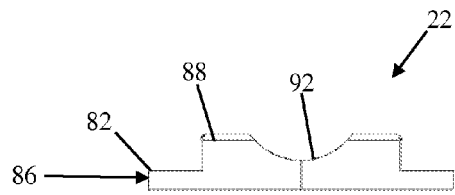
Figure 15:
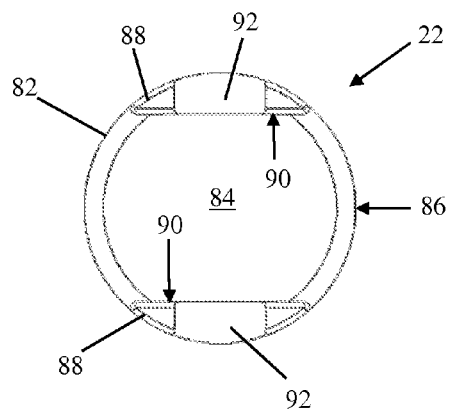

Referring now to FIGS. 13-15, the washer 22 will now be described. The washer 22 includes a solid ring 82 with a through passage 84 configured to receive the undercut recesses 70 of the rod-receiving member 20. The washer 22 has an outer surface 86 having a generally circular cross-section. The washer 22 further includes a pair of raised protrusions 88 positioned on opposing sides of the through passage 84. The raised protrusions 88 each have a generally planar interior surface 90. The remaining interior surfaces of the washer 22 have an arcuate shape. In this manner, the peripheral shape of the through passage 84 is complimentary to the peripheral shape of the rod-receiving member 20, allowing for a snug mating of the rod-receiving member 20 and the washer 22. The raised protrusions 88 include a pair of concave recesses 92 configured to seat the spinal rod 14 therein. The washer 22 sits between the rod-receiving member 20 and the fixation body 16. When the anchor assembly 12 is in an unlocked state, the washer 22 is able move with the rod-receiving member 20 (but does not move relative to the rod-receiving member 20), allowing multiple degrees of movement (e.g. rotational and translational movement) of the washer 22 and rod-receiving member 20 relative to the fixation body 16. When the spinal rod 14 is locked down using the rod lock 24, the spinal rod 22 sits in the concave recesses 92 on either side of the washer 22. The recesses 92 are concave in the embodiment shown and described herein, but could be any shape (e.g. V-shaped) that allows of sufficient seating of the spinal rod 14. As will be explained below, when the spinal rod 16 is locked to the washer 22 (by the rod lock 24), the washer 22 is forced into the fixation body 16 which creates a friction lock between the washer 22 and the fixation body 16. This also forces the flange 64 on the rod-receiving member 20 to be forced against the overhangs 52 of the recess 44 of the fixation body 16, increasing the friction lock. The created friction lock prevents any movement (e.g. rotational and/or translational) of the rod-receiving member 20 in the locked state. Thus the washer 22 allows the spinal rod 16 and rod-receiving member 20 to be locked simultaneously. It is also contemplated that the rod-receiving member 20 may be locked prior to locking the rod. This locking prior to rod locking may be temporary or permanent and may be accomplished, for example, with a tool that engages around or through the guide to interact with the washer and/or rod-receiving member, or through a feature built into the guide itself that interacts with the washer and/or rod-receiving member. By way of example the tool or feature may include, among others, a press, swedge, or crimp. Locking the rod-receiving tulip prior to rod insertion (or after rod insertion but prior to rod locking) allows the surgeon to apply force to the vertebra through the guide assembly which can be utilized to accomplish derotation maneuvers, compression, distraction, or other manipulations to change the alignment of the vertebrae.

Figure 16:
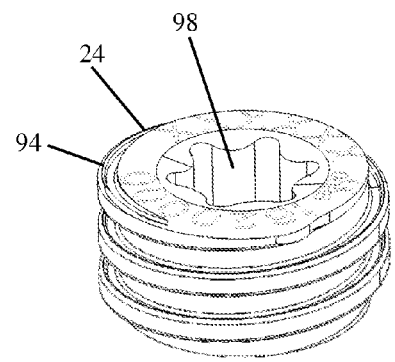
FIGS. 16-18 are perspective, side plan, and top plan views, respectively, of a rod lock member forming part of the anchor assembly of FIG. 2.
Figure 18:
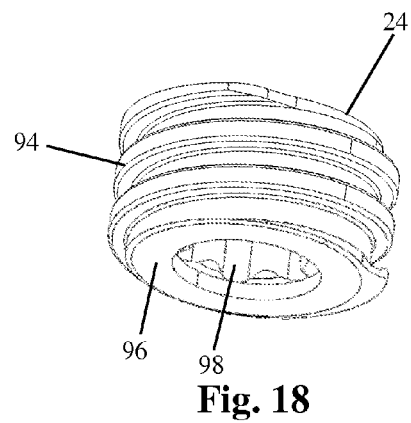

Referring to FIGS. 16-18, the rod lock 24 is a setscrew-type locking device that has a generally cylindrical shape and is received within the rod channel 60 of the rod-receiving member 20. The rod lock 24 is equipped with a guide and advancement feature 94, such as by way of example, a helically wound flange feature disposed around the outer surface of the rod lock 24. The guide and advancement feature 94 mates with the complementary rod lock guide and advancement feature 72 on the rod-receiving member 20, described above. The rod lock 24 further includes a rod-engaging distal surface 96 adapted to contact the spinal rod 14 during use. By way of example only, the distal surface 96 is shown as being generally planar, however the distal surface 96 may have other configurations (e.g. convex or concave) without departing from the scope of this disclosure. The rod lock 24 also includes a central aperture 98 configured for mating with an insertion and drive tool (not shown) to apply sufficient torque to lock the anchor assembly 12 together.

Figure 19:
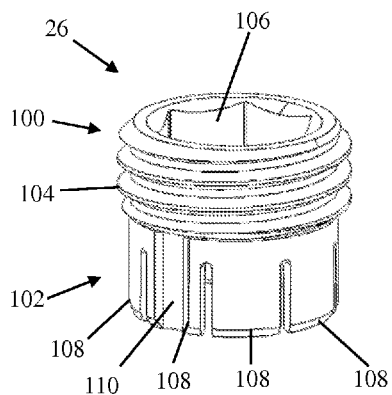
FIGS. 19-21 are perspective, side plan, and bottom plan views, respectively, of an anchor lock member forming part of the anchor assembly of FIG. 2.
Figure 20:
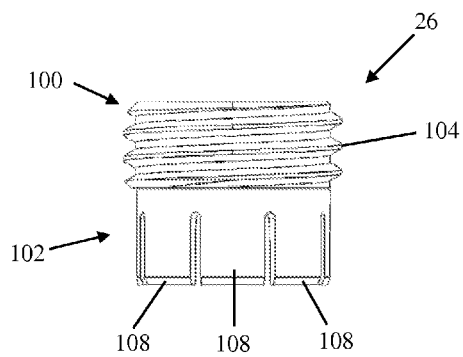
Figure 21:
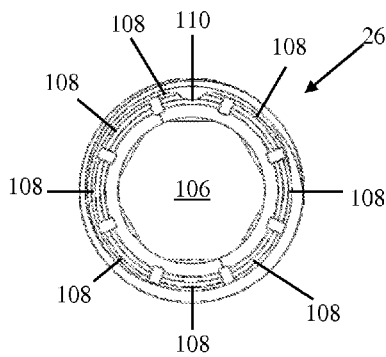

Referring to FIGS. 19-21, the anchor lock 26 is used to lock the bone anchor 18 to the fixation body 16. By way of example, the anchor lock 26 is generally cylindrical in shape and includes a first region 100 configured to engage the fixation body 16 and a second region 102 configured to engage the head 114 of the bone anchor 18. While shown herein as a single piece, anchor lock 26 may be have a multi-piece configuration in which the first region 100 and second region 102 are separate pieces (such that the second region 102 is rotationally uncoupled from first region 100). In the example described herein, the first region 100 includes a helical thread 104 configured to threadedly engage the threaded region 40 of the aperture 38 of the fixation body 16. The threaded engagement allows the anchor lock 26 to be rotationally advanced into the aperture 38 to lock the bone anchor 18 to the fixation body 16. The first region 100 further includes a central aperture 106 configured to receive an insertion and driver tool (not shown). The second region 102 includes a series of flexible extensions 108 distributed radially about the circumference of the anchor lock 26. As will be explained below, the flexible extensions 108 are capable of being deflected inward by the conical taper 42 of the aperture 38 as the anchor lock 26 is advanced into the aperture 38. Once deflected by the conical taper 42, the flexible extensions 108 collectively form an aperture having a diameter that is smaller than the diameter of the head 114 of the bone anchor 18, which effectively prevents the head 114 from exiting the aperture 38. Thus, the bone anchor 18 is locked to the fixation body 16. Other embodiments of an anchor lock 26 may include a rotation clamp, split ring and set screw, or two-piece clamp and set screw. The internal features of the anchor lock shown include a spherical surface to hold anchor and flats to allow the anchor to go into anchor lock with ease during insertion. Additionally, the anchor lock 26 may be provided with a mechanism to prevent rotation of the second region 102 during insertion. For example, at least one of the flexible extensions 108 may include a recess 110 configured to mate with a ridge 112 formed within the aperture 38 (FIG. 6).

Figure 22:
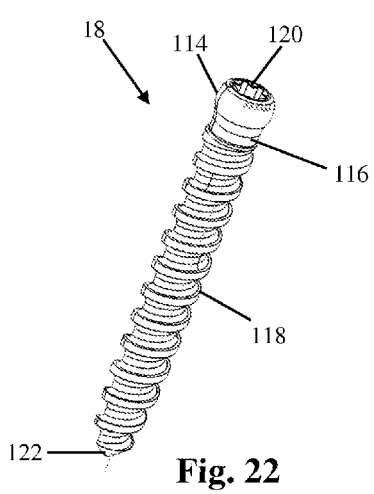
FIGS. 22-23 are perspective and plan views, respectively, of a bone anchor forming part of the anchor assembly of FIG. 2.
Figure 23:
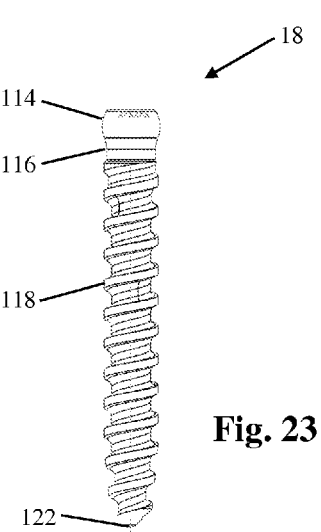

Referring to FIGS. 22-23, the bone anchor 18 includes a head portion 114, a neck portion 116, and a threaded shaft 118. The head portion 114 includes an engagement recess 120 formed therein that is configured to engage with a suitable driver instrument (not shown). The neck portion 116 is a generally smooth (e.g. non-threaded) surface extending circumferentially around the bone anchor 18. The diameter of the neck portion 116 is smaller than the largest diameter of the head portion 114, which creates a space to receive the deflected distal ends of the flexible extensions 108 of the anchor lock 26 during use. The threaded shaft 118 extends distally from the neck region 116 and may be any length suitable to achieve purchase in the bone. Optionally, the distal end 122 of the bone anchor 18 may include a sharp and retractable element (not shown) that can be maintained within the distal end 122 and exposed only when starting the bone anchor 18 into bone. The sharp end allows the bone anchor 18 to be used without first forming a pilot hole. Retracting the sharp end into the shank allows the bone anchor 122 to be positioned bicortically, that is the distal end 122 can rest right at the edge of the vertebral body without worrying that that the sharp tip may extend outside the periphery of the vertebral body and contact sensitive tissue (e.g. segmental vessels). Alternatively, the bone anchor 18 may be cannulated to allow for the use of a K-wire (for example) to aid in placement of the bone anchor 18 within the target site.

FIGS. 24-27 illustrate a sequential dilation system 130 configured for use to introduce components of the surgical fixation system 10 to the surgical target site. Referring first to FIG. 24, and initial dilator 132 is shown. The initial dilator 132 comprises an elongated cannulated body 134. The distal end 136 is tapered to facilitate safe passage through tissue lying above the spine. The distal end may also include an electrode 138 to facilitate passage through tissue nerve occupied tissue. The electrode 138 is configured for connection with a neuromonitoring system, for example of the type shown and described in U.S. Pat. No. 8,255,045, issued Aug. 28, 2012, for detecting the presence and direction of nerves near the distal end of the initial dilator. Near proximal end 139 a proximal connector region 140 is configured to receive an electrical connector (for example, not shown) to connect the dilator to the neuromonitoring system. The main body of the initial dilator 134 is insulated (except for connector region 140 and electrode 138) to prevent current shunting. Within the elongated cannulation 142, the initial dilator 132 includes an integrated needle 144 that may be deployed into the bone to hold the position of the initial dilator 132 in the desired location against the spine. A spring (not shown) maintains the needle in a first position in which a sharp distal end of the needle is contained within the main body cannulation 142 in order to protect the tissue during dilator passage. Once docked against the vertebral body, the needle 144 is depressed, advancing the distal end beyond the main body such that it engages into the vertebral body. Friction between the needle and the vertebral body prevents the needle 144 from returning to the original biased position.

With reference to FIGS. 25 and 26 now, the remainder of the sequential dilation system 130 includes a series of additional dilators. According to the example embodiment shown, the additional dilators include a fixation dilator 146, a transition dilator 174, and a final dilator 164. The fixation dilator 146 has an elongated generally cylindrical body 148 having a main lumen 150 extending therethrough for passage over the initial dilator. The diameter of the main lumen 150 is also such that the bone anchor 18 (and a tap, if utilized) can pass therethrough for implantation into the vertebra. A pair of separate fixation lumens 152 may extend along the exterior of the fixation dilator and are dimensioned to allow passage of fixation elements (e.g. K-wires, pins, etc. . . . ) to hold the position of the fixation dilator 146 in the desired location against the spine, especially during bone anchor 18 insertion. Fixation dilator 146 also includes a radiopaque marker 154 (e.g. a metal ring situated in a groove or multiple (e.g. 4) internal metal pins) near the distal end 156 of the dilator. The radiopaque marker 154 allows the user to intraoperatively view (e.g. via x-ray, fluoroscopy, or other suitable methods) the location of the distal end 156 of the dilator 146 to facilitate proper placement of the bone anchor 18. The distal end of the fixation dilator may also include an electrode 158 configured for connection with a neuromonitoring system. A proximal connector region 160 near proximal end 162 is configured to receive an electrical connector of the neuromonitoring system, the dilator 146 being insulated everywhere but the proximal connector 160 and the electrode 158 in order to prevent current shunting. The electrode 158 is preferably positioned such that it corresponds to the position of the fixation lumens 152. Thus the surgeon can ensure the area below the distal fixation lumen openings is free of nerves before advancing the fixation element. By way of example, the electrode 158 is positioned directly between (and below) the two fixation lumens 152. FIG. 27 illustrates an alternate embodiment of fixation dilator 146 which includes only a single fixation lumen 152 and the electrode 158 is positioned directly below the fixation lumen 152.

The final dilator 164 includes a main body 166 with a lumen 168 extending from proximal end 170 to a distal end 172. The lumen 168 dimensioned such that the final dilator can advance to the spine over the transitional dilator 174 and such that the fixation body 16 can pass therethrough for implantation to the vertebra. The footprint of the final dilator 164 is shaped to correspond to the fixation body 16, and thus, according to the example embodiment shown, is generally oblong in cross-sectional shape. The transition dilator 174 also includes a main body 176 and a lumen 178 extending therethrough from a proximal end 180 to a distal end 182. The transition dilator serves as a transition from the generally cylindrical shape of the initial 132 and fixation 146 dilators to the generally oblong shape of the final dilator 164. The lumen 178 then is generally cylindrical (with recesses to accommodate the fixation lumens) and dimensioned to pass over the fixation dilator 146. The main body 176 includes an asymmetric taper 184 that increases from a dimension just larger than the fixation dilator 146 at the very distal end 182 to a dimension just smaller than the lumen 168 of the final dilator 164.

Figure 29:
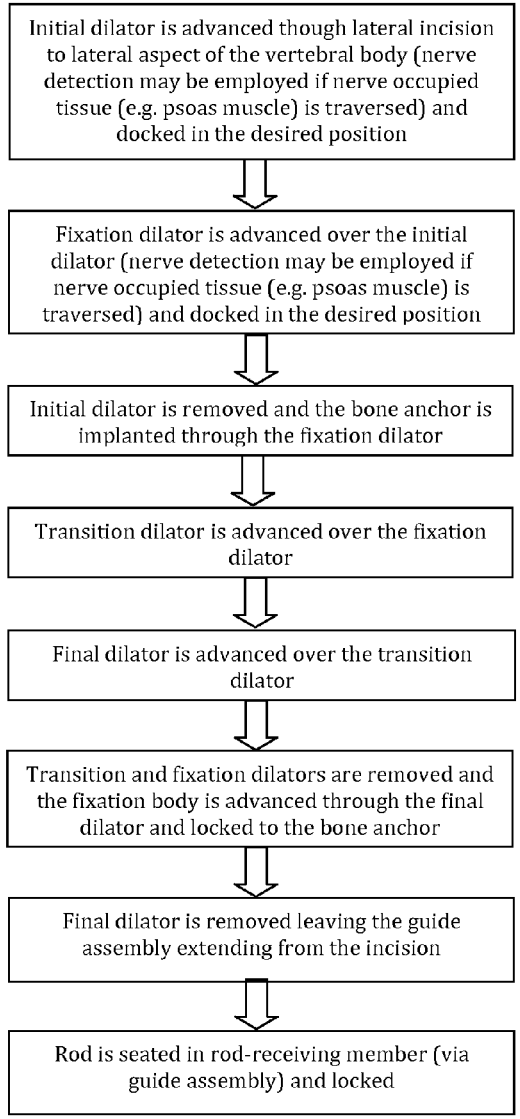
FIG. 29 is a flowchart denoting the steps of an example method for implanting an anchor assembly of FIG. 1 onto the lateral aspect of a vertebral body.

With reference to FIGS. 28 and 29, a preferred method for installing the anchor assemblies on the anterior column of the spine is described. First, the initial dilator 132 is advanced through a lateral incision to the desired position on the lateral aspect of the vertebral body. If the path of the dilator 132 will traverse nerve occupied tissue, for example, when traversing the psoas muscle to access lower levels of the lumbar spine, a neurophysiology monitoring system may be connected to the initial dilator 132 for nerve detection during advancement. When the dilator is correctly positioned on the vertebral body, the needle 144 is depressed to anchor the needle in the vertebral body and dock the initial dilator in place. The fixation dilator 146 is advanced over the initial dilator, again, nerve detection may be employed if nerve occupied tissue (e.g. psoas is traversed. A k-wire(s) can then be advanced through the fixation lumen(s) and anchored into the vertebral body to dock the fixation dilator. Once the fixation dilator is docked the initial dilator is removed and the bone anchor is advanced through the lumen 150 and anchored to the vertebral body. The transition dilator 174 is then advanced to the vertebra over the fixation dilator followed by the final dilator 164. With the final dilator in place, the transition dilator 174 and fixation dilator 146 are removed. The fixation body 16 is then advanced through the lumen 168 of the final dilator until the Transition and fixation dilators are removed and the fixation body is advanced through the final dilator and locked to the bone anchor head 114 is fully received in the aperture 38 of the fixation body and anterior protrusions 32 are anchored in the vertebral body. The anchor is then locked to the fixation body by engaging the threads of the anchor lock 26 with the threads 40 in the aperture 28 to advance the lock until the flexible extensions 108 are deflected by the conical taper 42 and capture the head 114 of the bone anchor 18. The final dilator is removed leaving the guide assembly attached to the rod-receiving member and extending out of the incision. Once all fixation assemblies 12 are implanted a rod 14 is advanced into each rod-receiving member 20, as facilitated by the guide assemblies 200, and locked in position with rod locks 24.

The vertebral fixation system 10 is generally utilized to augment a corrective procedure performed on the spine, such as, a spinal fusion. In particular, the spinal fixation system 10 may be used to provide fixation after lateral interbody fusion performed. The spinal fixation system 10 could also be used, for example, to provide fixation after a lateral corpectomy is performed. The lateral interbody fusion procedure is entails creating a lateral access corridor to the disc, performing a discectomy, and implanting a fusion implant into disc space created by the discectomy. An example technique for accessing the lateral spine to perform a fusion is described in U.S. Pat. No. 7,905,840 entitled "Surgical Access System and Related Methods," issued Mar. 15, 2011. When utilizing the spinal fixation system 10, the fusion (or other corrective procedure, e.g. corpectomy) is completed on each level and then the fixation system 10 is applied utilizing the original access incision(s) where possible to limit the amount of incising required to complete the entire surgical procedure (e.g. fusion and fixation).

With reference to FIGS. 30 and 31, one example method for performing a single level lateral fusion procedure with the fixation system 10 is described. First, a lateral access corridor is created through a first incision and fusion is procedure is complete, as is described by way of example in the '840 patent. If the disc is at a level where the path to the disc will traverse nerve occupied tissue, for example, the psoas muscle, the creation of the operative corridor is preferably completed with the aid of neurophysiology monitoring for nerve detection. After the fusion work on the disc is complete, the retractor can be moved relative to the spine (i.e. without removing from the incision) such that the corridor through the retractor rests over the first vertebra. The first fixation assembly 12 can then be implanted through the operative corridor. Preferably, though not necessarily, the first fixation assembly is implanted using the sequential dilation system 130. If the operative corridor traverses the psoas, rather than moving the retractor, the retractor may be removed and the initial dilator 132 may be advanced through the first incision (which can then be moved to one side and positioned over the first vertebral body) and establish a new path (aided by neurophysiology monitoring) through the psoas for subsequent dilation and anchor assembly implantation (as previously described). The dilation system 30 is removed leaving the guide assembly 200 extending from the first incision. Again through the first incision (which can be moved to the second side and positioned over the second vertebral body), the second anchor assembly 12 is implanted using the dilation system 130. The final dilator 164 is removed such that both guide assemblies 200 extend out of the first incision. A rod 14 is then advanced into each rod-receiving member 20, as facilitated by the guide assemblies 200, and locked in position with rod locks 24. The guide assemblies are detached and removed and the incision closed. FIG. 31 depicts the completed single level spinal construct using the spinal fixation system 10.

With reference to FIGS. 32 and 33, one example method for performing a multilevel lateral fusion procedure with the fixation system 10 is described. For the sake of clarity, the example method will be described (by way of example only) as a three level fusion from L3 to T12. Accordingly, each of the L2/3, L1/2, and T12/L1 disc will be fused and the fixation system 10 will span from the L3 vertebral body to the T12 vertebral body. To begin, a first lateral incision is made over the L2 body. The incision is moved over the L2/3 disc space and a lateral access corridor is created and fusion procedure completed. The retractor is moved relative to the spine without withdrawing from the incision and positioned over the L1/L2 disc space and the fusion procedure is completed at that level. After the fusion work on the L1/L2 disc is complete, a second lateral incision may be made over the T12 body. The incision is moved over the T12/L1 disc space and a lateral access corridor is created and fusion procedure completed. If the access path to one or more of the disc spaces is to traverse the psoas, rather than simply moving the retractor, it is preferable that the retractor be withdrawn and a new path through the psoas be created (utilizing the same incision however) with the aid of neurophysiology monitoring and sequential dilation.

Once the fusion procedure is complete at each level, the fixation system 10 can be constructed. To do so, the dilation system 130 is utilized through the first incision to implant a first anchor assembly 12 on the L3 vertebral body with guide assembly 200 attached and extending out of the first incision. The first incision is then stretched over to the L2 vertebral body and a dilator system 130 is used to implant a second anchor assembly 12 on the L2 body with a guide assembly 200 attached and also extending out of the first incision. A third anchor assembly 12 is implanted on the L1 vertebral body using a dilator system 130. Depending on the patients skin, fascia, and anatomy, the surgeon can target the L1 body either the first or the second incision. A guide assembly 200 is left attached to the third anchor assembly 12 and extending out of the incision used (i.e. first or second). Finally, using a dilator system 30 through the second incision, a fourth anchor assembly 12 is implanted in the T12 vertebral body with a guide assembly 200 attached and extending out of the second incision. Once all anchor assemblies 12 are implanted, a rod 14 is advanced into each rod-receiving member 20, as facilitated by the guide assemblies 200, and locked in position with rod locks 24. The guide assemblies are detached and removed and the incision closed. FIG. 33 depicts the completed multilevel spinal construct using the spinal fixation system 10.

Figure 34:
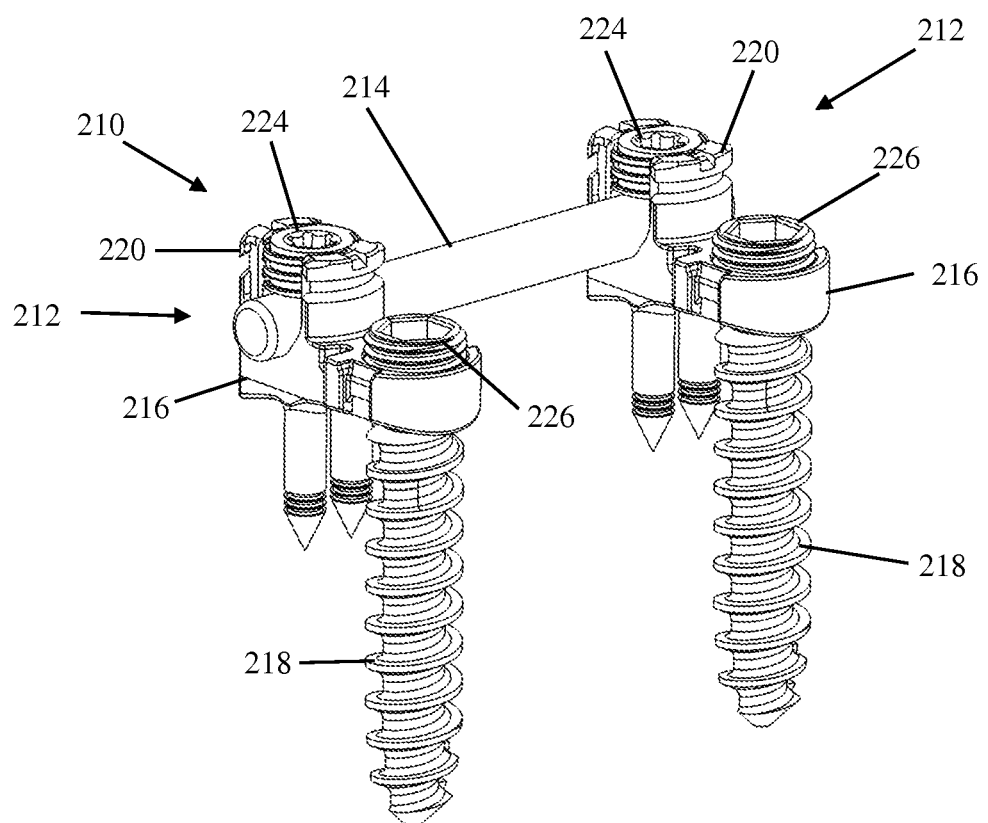
FIG. 34 is a perspective view of a second example of a vertebral fixation system according to a second embodiment.

FIG. 34 illustrates an example of a surgical fixation system 210 according to an alternative embodiment. The vertebral fixation system 210 includes at least a pair of anchor assemblies 212 connected by a spinal rod 214. Each anchor assembly 212 includes a fixation body 216, a bone anchor 218, a rod-receiving member 220, rod lock 224, and an anchor lock 226. The fixation system 210 differs from the fixation system 10 in one major aspect. Whereas the fixation system 10 described above allows for movement of the rod-receiving member 20 and washer 22 prior to rod insertion and final tightening, the fixation system 210 has a rod-receiving member 220 that is integrally formed with the fixation body 216 and this is unable to move. Consequently, there is no washer member corresponding to the washer 22 of the fixation system 10 due to the lack of movement. The fixation system 210 is identical to the fixation system 10 described above in virtually every other way, and any of those features described above (not related to movement of the rod-receiving member) may be applied to the fixation system 210 without departing from the scope of the disclosure.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

We claim:

1. A spinal fixation system configured for implantation on a lateral aspect of a human spine for immobilizing at least two vertebral bodies relative to one another, comprising:
   an elongated generally cylindrical spinal rod having a size sufficient to span the distance between a first anchor assembly implanted in a first vertebral body and a second anchor assembly implanted in a second vertebral body;
   at least two adjustable anchor assemblies, each adjustable anchor assembly implantable on a vertebral body and configured to adjustably receive a portion of the spinal rod and thereafter further receive a rod locking element that when applied alters the state of the anchor assemblies from the adjustable state to a locked state, each anchor assembly comprising:
      an anchor element configured to anchor the anchor assembly to the vertebral body, the anchor element including an elongated threaded shaft for gaining purchase within a vertebra and a head element positioned proximally from the shaft, the head element separated from the shaft by a neck region, the neck region having a diameter less than the largest diameter of the head element;
      a fixation base having an anchor aperture configured to receive the head portion and at least a portion of the neck region of the anchor element, the aperture further configured to receive at least a portion of an anchor locking element;
      an anchor locking element moveably coupled with the fixation base and configured to retain a portion of the anchor element to prevent disassociation of the anchor element from the fixation base;

a rod receiving element coupled with the fixation base and initially moveable relative to the fixation base, the rod receiving element comprising a base portion including a retaining flange having a generally T-shaped cross-section; and a rod locking element introducible to the rod receiving element after coupling of the spinal rod and the rod receiving element, the rod locking element having a contact surface that contacts the spinal rod and exerts a force on the spinal rod that locks the spinal rod to the rod receiving element while simultaneously locking the previously moveable rod receiving element in position relative to the fixation base.

2. The spinal fixation system of claim 1, wherein the fixation base includes at least one supplemental anchor element extending generally perpendicularly from a bottom surface of the fixation base, the supplemental anchor element configured to penetrate a vertebral body.

3. The spinal fixation system of claim 1, wherein the anchor locking element is moveable within the anchor aperture from a first position in which the anchor element head element is able to move into and out of the anchor aperture to a second position in which the anchor element head element is retained within the anchor aperture by a portion of the anchor locking element, thereby locking the fixation base to the anchor element.

4. The spinal fixation system of claim 1, wherein the anchor aperture has a bottom opening having a diameter greater than the largest diameter of the anchor element head element.

5. The spinal fixation system of claim 4, wherein the anchor aperture has a inner circumferential conically tapered surface configured to inwardly deflect at least a portion of the deflectable extensions of the anchor locking element.

6. The spinal fixation system of claim 5, wherein advancement of the anchor locking element into the anchor aperture causes the deflectable extensions to contact the circumferential conically tapered surface and deflect inward.

7. The spinal fixation system of claim 6, wherein the inwardly deflected deflectable extensions act in concert to create a locking aperture having a diameter that is smaller than the largest diameter of the anchor element head element but larger than the diameter of the anchor element neck element, thereby effectively locking the fixation body to the bone anchor element.

8. The spinal fixation system of claim 1, wherein the wherein the base portion includes and a pair of opposing upstanding arms that act in concert to form a rod channel configured to receive the spinal rod therein.

9. The spinal fixation system of claim 1, wherein the retaining flange has a generally circular shaped footprint.

10. The spinal fixation system of claim 9, wherein the fixation base has an elongated recess formed in an upper facing surface, the elongated recess configured to moveably receive the retaining flange of the rod receiving element therein.

11. The spinal fixation system of claim 10, wherein the recess further includes a pair of overhangs configured to prevent movement of the retaining flange away from the fixation base.

12. The spinal fixation system of claim 11, wherein the retaining flange is sized and configured to rotate and translate within the recess.

13. A method for performing spine surgery, comprising:
establishing a minimally invasive operative corridor to a spinal target site, the spinal target site comprising at least a portion of a lateral aspect of a first vertebral body and at least a portion of a lateral aspect of a second vertebral body, the first and second vertebral bodies being adjacent one another;

implanting a first bone anchor in the lateral aspect of the first vertebral body, the first bone anchor including an elongated threaded shaft for gaining purchase within a vertebra and a head element positioned proximally from the shaft, the head element separated from the shaft by a neck region, the neck region having a diameter less than the largest diameter of the head element;

providing first and second fixation assemblies, the each of the first and second fixation assemblies including a fixation base, an anchor lock, and a rod housing, the fixation base having an anchor aperture configured to receive the head portion and at least a portion of the neck region of the bone anchor, the anchor aperture further configured to receive at least a portion of the anchor lock, the anchor lock moveably coupled with the fixation base and configured to retain a portion of the bone anchor to prevent disassociation of the bone anchor from the fixation base, the rod housing moveably coupled with the fixation base, the rod housing configured to receive a portion of a spinal rod therein;

implanting the first fixation assembly in the lateral aspect of the first vertebral body by advancing the first fixation assembly along the operative corridor until a lower bone engaging surface on the first fixation assembly contacts the vertebral body and the head element of the first bone anchor is received within the anchor aperture of the first fixation assembly;

actuating the anchor lock on the first fixation assembly to effect locking of the first bone anchor to the fixation base of the first fixation assembly;

implanting a second bone anchor in the lateral aspect of the second vertebral body, the second bone anchor including an elongated threaded shaft for gaining purchase within a vertebra and a head element positioned proximally from the shaft, the head element separated from the shaft by a neck region, the neck region having a diameter less than the largest diameter of the head element;

implanting the second fixation assembly in the lateral aspect of the second vertebral body by advancing the second fixation assembly along the operative corridor until a lower bone engaging surface on the second fixation assembly contacts the vertebral body and the head element of the second bone anchor is received within the anchor aperture of the second fixation assembly;

actuating the anchor lock on the second fixation assembly to effect locking of the second bone anchor to the fixation base of the second fixation assembly;

introducing a spinal rod segment such that a first portion of the spinal rod segment is placed within the rod housing of the first fixation assembly and a second portion of the spinal rod segment is placed within the rod housing of the second fixation assembly;

introducing a first rod lock element to the rod housing on the first fixation assembly and advancing the first rod lock element along the rod housing until a rod contact surface on the first rod lock element contacts the spinal rod, and further tightening the first rod lock element to lock the first spinal rod segment to the first anchor assembly and simultaneously causing the rod housing to lock in place relative to the fixation base of the first fixation assembly;

introducing a second rod lock element to the rod housing on the second fixation assembly and advancing the second rod lock element along the rod housing until a rod contact surface on the second rod lock element contacts the spinal rod, and further tightening the second rod lock element to lock the second spinal rod segment to the second anchor assembly and simultaneously causing the rod housing to lock in place relative to the fixation base of the second fixation assembly; and closing the minimally invasive operative corridor.

14. The method of claim 13, wherein the minimally invasive operative corridor is established using a lateral transpsoas approach.

15. The method of claim 13, comprising the further step of adjusting the first fixation assembly by translating the rod housing of the first fixation assembly relative to the fixation base of the first fixation assembly to accommodate the introduction of the spinal rod segment.

16. The method of claim 15, comprising the further step of adjusting the first fixation assembly by rotating the rod housing of the first fixation assembly relative to the fixation base of the first fixation assembly to accommodate the introduction of the spinal rod segment.

17. The method of claim 13, comprising the further step of adjusting the first fixation assembly by rotating the rod housing of the first fixation assembly relative to the fixation base of the first fixation assembly to accommodate the introduction of the spinal rod segment.

18. The method of claim 17, comprising the further step of adjusting the first fixation assembly by translating the rod housing of the second fixation assembly relative to the fixation base of the second fixation assembly to accommodate the introduction of the spinal rod segment.

19. The method of claim 13, comprising the further step of adjusting the first fixation assembly by rotating the rod housing of the first fixation assembly relative to the fixation base of the first fixation assembly to accommodate the introduction of the spinal rod segment.

20. The method of claim 19, wherein the fixation base of the first fixation assembly includes an elongated recess formed in an upper facing surface, the elongated recess configured to moveably receive the retaining flange of the rod housing therein.

21. The method of claim 13, wherein the rod housing of the first fixation assembly includes a retaining flange having a generally T-shaped cross-section.

* * * * *